United States Patent
Rüegg

(10) Patent No.: US 7,196,038 B1
(45) Date of Patent: Mar. 27, 2007

(54) HERBICIDAL COMPOSITION

(75) Inventor: Willy T. Rüegg, Greensboro, NC (US)

(73) Assignee: Syngenta Crop Protection, Inc., Greensboro, NC (US)

( * ) Notice: Subject to any disclaimer, the term of this patent is extended or adjusted under 35 U.S.C. 154(b) by 257 days.

(21) Appl. No.: 10/476,068

(22) PCT Filed: Apr. 26, 2002

(86) PCT No.: PCT/EP02/04645

§ 371 (c)(1),
(2), (4) Date: Oct. 24, 2003

(87) PCT Pub. No.: WO02/087322

PCT Pub. Date: Nov. 7, 2002

(30) Foreign Application Priority Data

Apr. 27, 2001  (CH) ..................... 770/01

(51) Int. Cl.
*A01N 25/32* (2006.01)
*A01N 43/56* (2006.01)
*A01N 43/80* (2006.01)
*A01N 43/84* (2006.01)

(52) U.S. Cl. .............. 504/105; 504/139; 504/149
(58) Field of Classification Search ........... 504/108, 504/282, 342, 105, 139, 149
See application file for complete search history.

(56) References Cited

U.S. PATENT DOCUMENTS

| 5,962,690 | A | * | 10/1999 | Benko et al. | 546/221 |
| 6,140,271 | A | * | 10/2000 | Turner et al. | 504/282 |
| 6,165,944 | A |  | 12/2000 | von Deyn et al. | |
| 6,534,444 | B1 | * | 3/2003 | Sievernich et al. | 504/128 |

FOREIGN PATENT DOCUMENTS

| WO | 9734485 | 9/1997 |
| WO | 9965314 | 12/1999 |
| WO | 0000031 | 1/2000 |
| WO | 0030447 | 6/2000 |
| WO | 0117350 | 3/2001 |
| WO | 0128341 | 4/2001 |

* cited by examiner

*Primary Examiner*—John Pak
(74) *Attorney, Agent, or Firm*—Rebecca Gegick

(57) ABSTRACT

A herbicidal composition that, in addition to comprising customary inert formulation adjuvants, comprises either: a) a compound of formula (I), wherein R is $C_1$–$C_2$alkyl or chlorine, $R_1$ is hydrogen or $C_1$–$C_4$alkyl and $R_2$ is $C_1$–$C_4$alkyl, or an agronomically acceptable salt of such a compound, and b) a synergistically effective amount of one or more compounds of formulae 2.1 to 2.51 and also an amount, effective for herbicide antagonism, of a safener, or: a) a compound of formula (I) and b) an amount, effective for herbicide antagonism, of a safener.

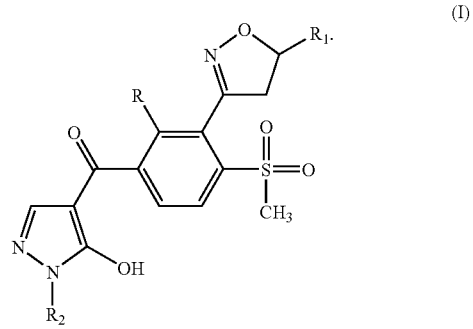

4 Claims, No Drawings

HERBICIDAL COMPOSITION

This application is a 371 of PCT/EP02/04645, filed on Apr. 26, 2002.

The present invention relates to a novel herbicidal composition comprising a herbicidal active ingredient combination that is suitable for the selective control of weeds in crops of useful plants, for example in maize crops. The invention relates also to a method of controlling weeds in crops of useful plants, and to the use of the novel composition for that purpose.

The compounds of formula I

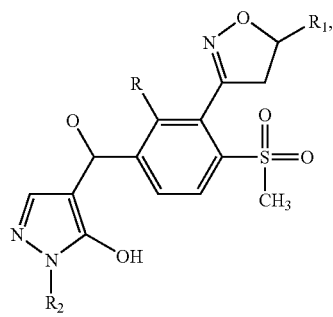

(I)

wherein R is $C_1$–$C_2$alkyl or chlorine, $R_1$ is hydrogen or $C_1$–$C_4$alkyl and $R_2$ is $C_1$–$C_4$alkyl, have herbicidal activity. The compounds of formula I and their preparation are described, for example, in WO 98/31681; mixtures of those compounds with herbicides are known from WO 99/65314.

Surprisingly, it has now been found that a combination of variable amounts of active ingredients, that is to say of an active ingredient of formula I with one or more of the active ingredients listed below, which are known and some of which are also commercially available, exhibits a synergistic action that is capable of controlling, both pre-emergence and post-emergence, the majority of weeds occurring especially in crops of useful plants.

There is therefore proposed in accordance with the present invention a novel synergistic composition for selective weed control that, in addition to customary inert formulation adjuvants, comprises as active ingredient a mixture of a) a herbicidally effective amount of a compound of formula I

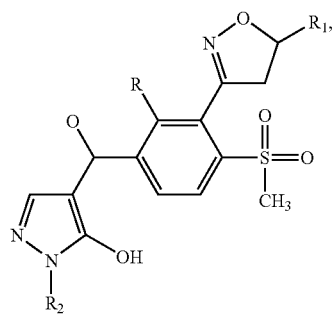

(I)

wherein R is $C_1$–$C_2$alkyl or chlorine, $R_1$ is hydrogen or $C_1$–$C_4$alkyl and $R_2$ is $C_1$–$C_4$alkyl, or an agronomically acceptable salt of such a compound, especially the sodium salt and ammonium salt, and b) a synergistically effective amount of one or more compounds selected from a compound of formula 2.1

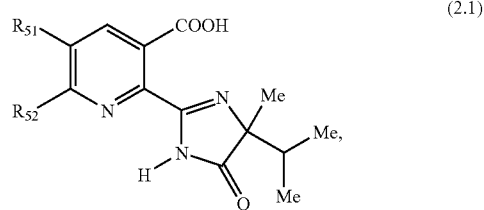

(2.1)

wherein $R_{51}$ is $CH_2$—OMe, ethyl or hydrogen;

$R_{52}$ is hydrogen or $R_{51}$ and $R_{52}$ together are the group —CH=CH—CH=CH—;

and a compound of formula 2.2

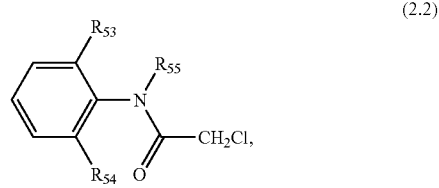

(2.2)

wherein $R_{53}$ is ethyl, $R_{54}$ is methyl or ethyl and $R_{55}$ is —CH(Me)—$CH_2$OMe, <S>—CH(Me)—$CH_2$OMe, $CH_2$OMe or $CH_2$O—$CH_2CH_3$;

and a compound of formula 2.3

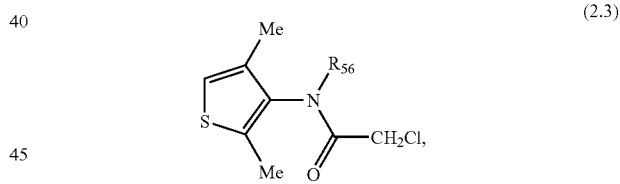

(2.3)

wherein $R_{56}$ is CH(Me)—$CH_2$OMe or <S>CH(Me)—$CH_2$OMe;

and a compound of formula 2.4

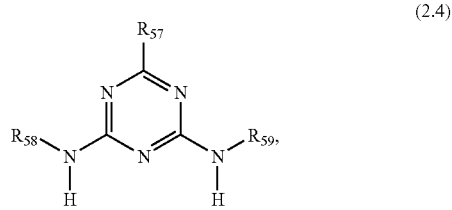

(2.4)

wherein $R_{57}$ is chlorine, methoxy or methylthio, $R_{58}$ is ethyl and $R_{59}$ is ethyl, isopropyl, —C(CN)($CH_3$)—$CH_3$ or tert-butyl;

and a compound of formula 2.5

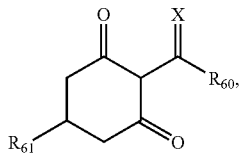
(2.5)

wherein $R_{60}$ is ethyl or n-propyl, $R_{61}$ is COO⁻ 1/2 Ca⁺⁺, —CH₂—CH(Me)S—CH₂CH₃ or the group

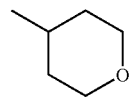

and X is oxygen, N—O—CH₂CH₃ or N—O—CH₂CH=CH—Cl;

and a compound of formula 2.6

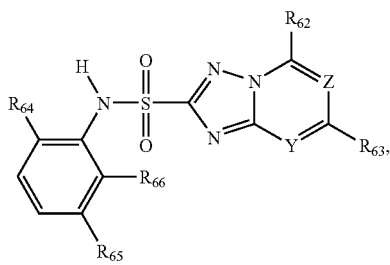
(2.6)

wherein $R_{62}$ is hydrogen, methoxy or ethoxy, $R_{63}$ is hydrogen, methyl, methoxy or fluorine, $R_{64}$ is COOMe, fluorine or chlorine, $R_{65}$ is hydrogen or methyl, Y is methine, C—F or nitrogen, Z is methine or nitrogen and $R_{65}$ is fluorine or chlorine;

and a compound of formula 2.7

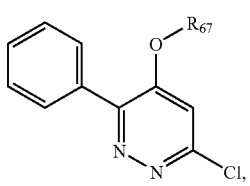
(2.7)

wherein $R_{67}$ is hydrogen or —C(O)—S-n-octyl;

and a compound of formula 2.8

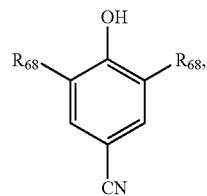
(2.8)

wherein $R_{68}$ is either bromine or iodine;

and a compound of formula 2.9

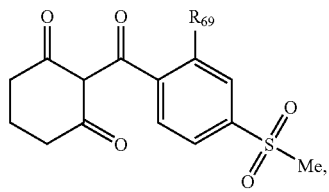
(2.10)

wherein $R_{69}$ is chlorine or nitro;

and a compound of formula 2.10

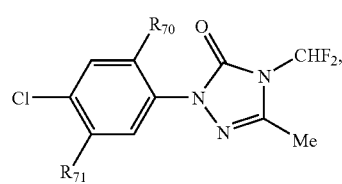
(2.10)

wherein $R_{70}$ is fluorine or chlorine and $R_{71}$ is —CH₂—CH(Cl)—COOCH₂CH₃ or —NH—SO₂Me;

a compound of formula 2.11

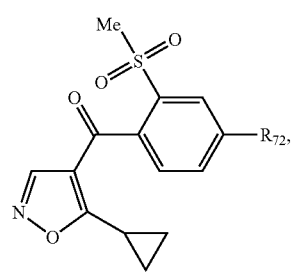
(2.11)

wherein $R_{72}$ is trifluoromethyl or chlorine;

and a compound of formula 2.12

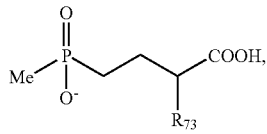
(2.12)

wherein $R_{73}$ is NH₂ or <S>NH₂;

and a compound of formula 2.13

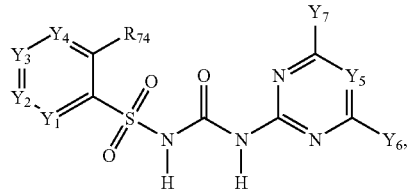
(2.13)

wherein $Y_2$ is nitrogen, methine, NH—CHO or N—Me, $Y_1$ is nitrogen, methine or C—I, $Y_3$ is methine, $Y_4$ is methine or $Y_3$ and $Y_4$ together are sulfur or C—Cl, $Y_5$ is nitrogen or methine, $Y_6$ is methyl, difluoromethoxy, trifluoromethyl or methoxy, $Y_7$ is methoxy or difluoromethoxy and $R_{74}$ is $CONMe_2$, COOMe, $COOC_2H_5$, trifluoromethyl, $CH_2$—$CH_2CF_3$ or $SO_2CH_2CH_3$, or a sodium salt thereof ("Me" being in each case the methyl group);

and the compound of formula 2.13.c

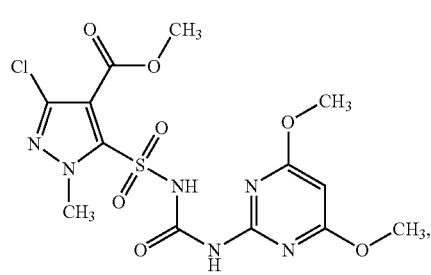
(2.13.c)

and the compound of formula 2.14

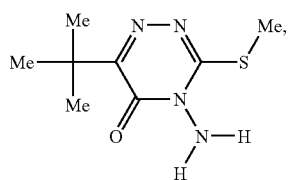
(2.14)

and the compound of formula 2.15

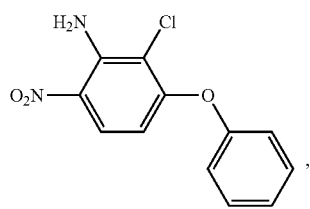
(2.15)

and the compound of formula 2.16

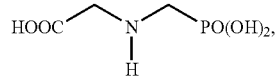
(2.16)

and the compound of formula 2.17

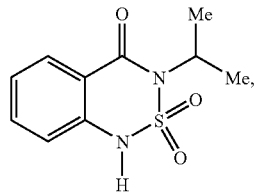
(2.17)

and the compound of formula 2.18

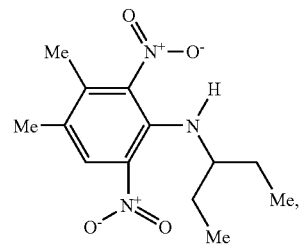
(2.18)

and the compound of formula 2.19

(2.19)

and the compound of formula 2.20

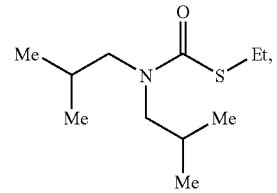
(2.20)

and the compound of formula 2.21 and the compound of formula 2.22 and the compound of formula 2.23 and the compound of formula 2.24 and the compound of formula 2.25 and the compound of formula 2.26 and the compound of formula 2.27 and the compound of formula 2.28 and the compound of formula 2.29
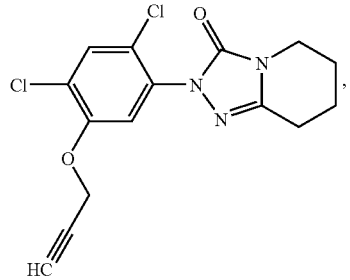
(2.29)
and the compound of formula 2.30
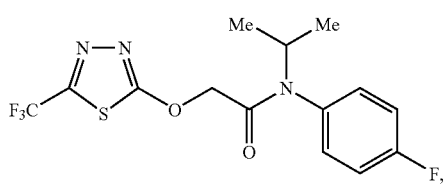
(2.30)
and the compound of formula 2.31
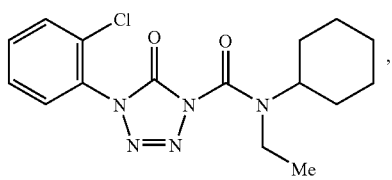
(2.31)
and the compound of formula 2.32
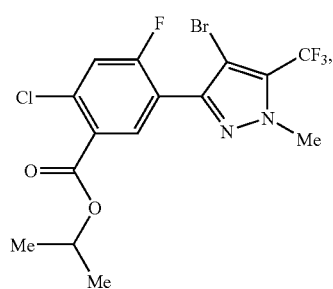
(2.32)
and the compound of formula 2.33
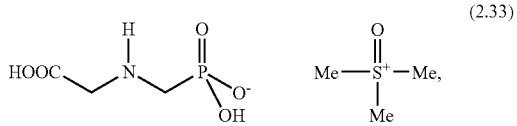
(2.33)
and the compound of formula 2.34
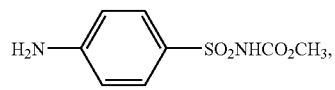
(2.34)
and the compound of formula 2.35
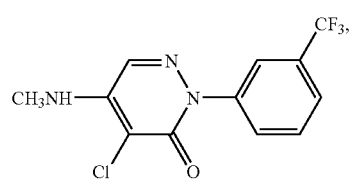
(2.35)
and the compound of formula 2.36
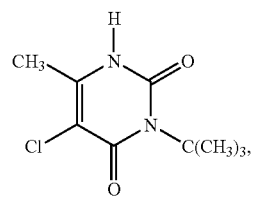
(2.36)
and the compound of formula 2.37
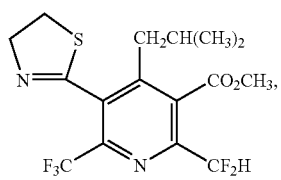
(2.37)
and the compound of formula 2.38
(2.38)

and the compound of formula 2.39
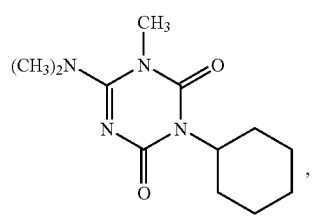
and the compound of formula 2.40
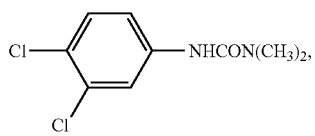
and the compound of formula 2.41
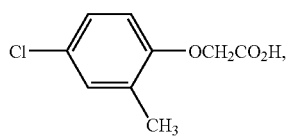
and the compound of formula 2.42
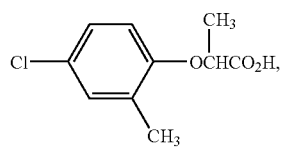
and the compound of formula 2.43
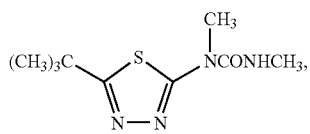
and the compound of formula 2.44
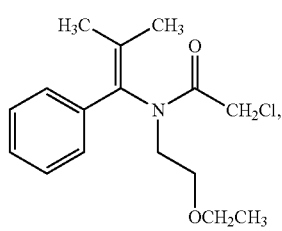
and the compound of formula 2.45
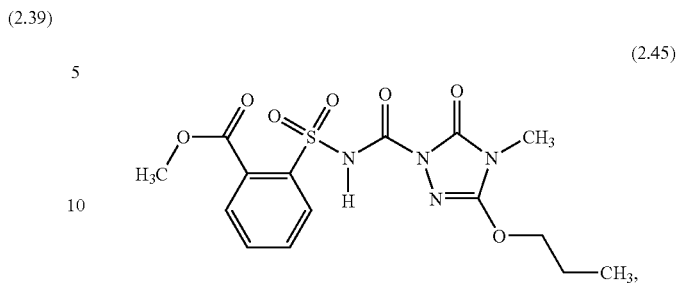
and the compound of formula 2.46
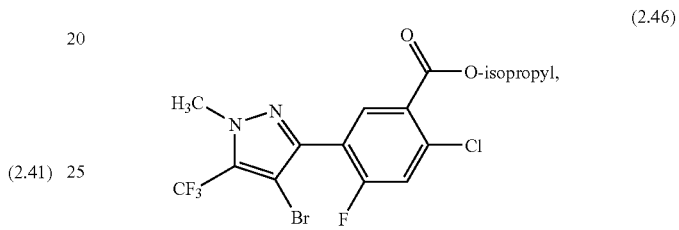
and the compound of formula 2.47
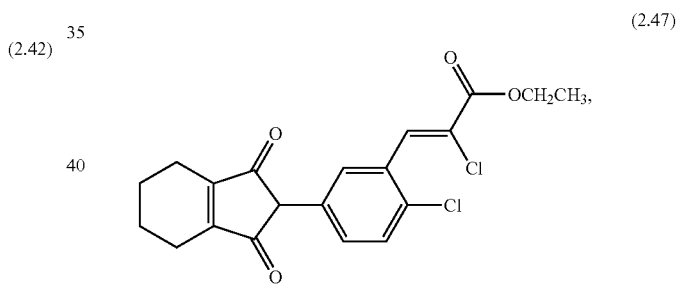
and the compound of formula 2.48
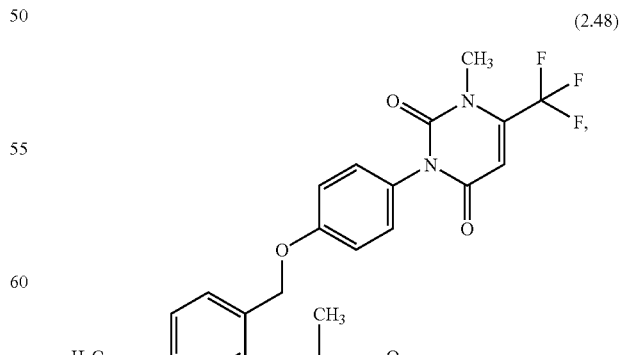

and the compound of formula 2.49

(2.49) [chemical structure: 2-acetylpyridine-3-carboxylic acid derivative with semicarbazone linked to 3,5-difluorophenyl]

and the compound of formula 2.50

(2.50) [chemical structure: tert-butyl carbamoyl triazolinone with isopropyl and amino substituents]

and the compound of formula 2.51

(2.51) [chemical structure: chloro-fluorophenyl pyridazinone with trifluoromethyl and ethoxycarbonylmethoxy substituents]

and c) an amount, effective for herbicide antagonism, of a compound selected from the compound of formula 3.1

(3.1) [chemical structure: 3-methyl-4-(dichloroacetyl)-benzoxazine]

and the compound of formula 3.2

(3.2) [chemical structure: 4,6-dichloro-2-phenylpyrimidine]

and the compound of formula 3.3

(3.3) [chemical structure: 1-ethyl-4-hydroxy-3-(tetrazolylcarbonyl)quinolin-2(1H)-one]

and the compound of formula 3.4

(3.4) [chemical structure: 1-(2,4-dichlorophenyl)-5-methyl-3,5-bis(ethoxycarbonyl)-4,5-dihydropyrazole]

and the compound of formula 3.5

(3.5) [chemical structure: N-(dichloroacetyl)-2,2-dimethyl-5-(2-furyl)oxazolidine]

and the compound of formula 3.6

(3.6) [chemical structure: 4-(carboxymethyl)-chroman-4-carboxylic acid]

and the compound of formula 3.7

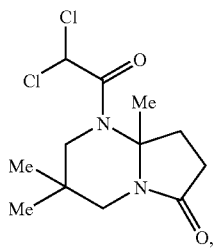
(3.7)

and the compound of formula 3.8

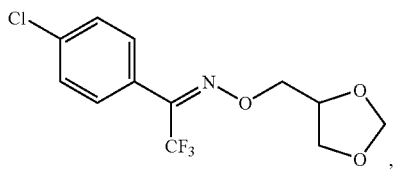
(3.8)

and of formula 3.9

 (3.9),

Cl$_2$CHCON(CH$_2$CH=CH$_2$)$_2$ and of formula 3.10

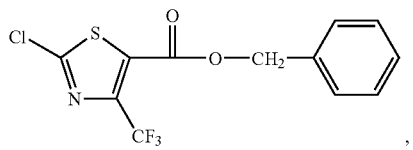
(3.10)

and of formula 3.11

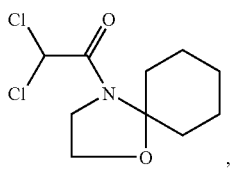
(3.11)

and of formula 3.12

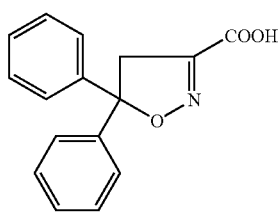
(3.12)

and its ethyl ester, and of formula 3.13

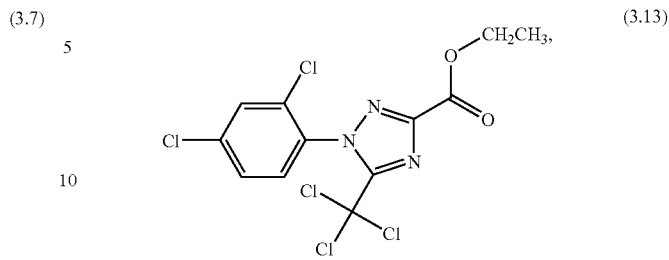
(3.13)

and of formula 3.14

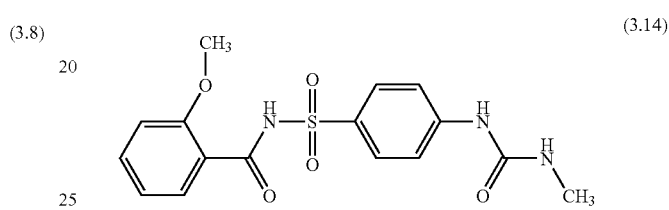
(3.14)

and of formula 3.15

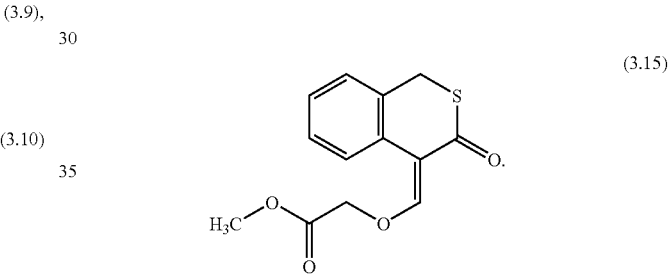
(3.15)

In the above formulae, "Me" is a methyl group.

The invention also includes the salts that the compounds of formula I are able to form with amines, alkali metal and alkaline earth metal bases or quaternary ammonium bases. Among the alkali metal and alkaline earth metal hydroxides used as salt formers, emphasis is to be given to the hydroxides of lithium, sodium, potassium, magnesium and calcium, but especially to those of sodium and potassium.

Examples of suitable amines for ammonium salt formation that come into consideration are ammonia as well as primary, secondary and tertiary $C_1$–$C_{18}$alkylamines, $C_1$–$C_4$hydroxyalkyl-amines and $C_2$–$C_4$alkoxyalkylamines, for example methylamine, ethylamine, n-propylamine, isopropylamine, the four butylamine isomers, n-amylamine, isoamylamine, hexylamine, heptylamine, octylamine, nonylamine, decylamine, pentadecylamine, hexadecylamine, heptadecylamine, octadecylamine, methyl-ethylamine, methyl-isopropylamine, methyl-hexylamine, methyl-nonylamine, methyl-pentadecylamine, methyl-octadecylamine, ethyl-butylamine, ethyl-heptylamine, ethyl-octylamine, hexyl-heptylamine, hexyl-octylamine, dimethylamine, diethylamine, di-n-propylamine, diisopropylamine, di-n-butylamine, di-n-amylamine, diisoamylamine, dihexylamine, diheptylamine, dioctylamine, ethanolamine, n-propanolamine, isopropanolamine, N,N-diethanolamine, N-ethylpropanolamine, N-butyl-ethanolamine, allylamine, n-butenyl-2-amine, n-pentenyl-2-amine, 2,3-dimethylbutenyl-2-amine, dibutenyl-2-amine, n-hexenyl-2-amine, propylenediamine, trimethylamine, triethyl-amine, tri-n-propylamine, triisopropylamine, tri-n-butylamine, triisobutylamine, tri-sec-butylamine, tri-n-amylamine, methoxyethylamine and ethoxyethylamine; heterocyclic amines, for example pyridine, quinoline, isoquinoline, morpholine, piperidine, pyrrolidine, indoline, quinuclidine and azepine; primary aryl amines, for example anilines, methoxyanilines, ethoxyanilines, o-, m- and p-toluidines, phenylenediamines, benzidines, naphthylamines and o-, m- and p-chloroanilines; but especially triethylamine, isopropylamine and diisopropylamine.

The alkyl groups appearing in the substituent definitions may be straight-chained or branched and are, for example, methyl, ethyl, n-propyl, isopropyl, n-butyl, sec-butyl, isobutyl or tert-butyl.

It is extremely surprising that the combination of the active ingredient of formula I with one or more active ingredients selected from formulae 2.1 to 2.51 in combination with safeners 3.1 to 3.15 exceeds the additive herbicidal effect on the weeds to be controlled that is to be expected in principle and thus broadens the range of action of the individual active ingredients especially in two respects: firstly, the rates of application of the individual compounds of formulae I and 2.1 to 2.51 are reduced while a good level of action is maintained and, secondly, the composition according to the invention achieves a high level of weed control also in those cases where the individual substances, in the low rates of application range, have become useless from the agronomic standpoint. The result is a considerable broadening of the spectrum of weeds and an additional increase in selectivity in respect of the crops of useful plants, as is necessary and desirable in the event of an unintentional overdose of active ingredient. The composition according to the invention, while retaining excellent control of weeds in crops of useful plants, also allows greater flexibility in succeeding crops.

The composition according to the invention can be used against a large number of agronomically important weeds, such as *Stellaria, Nasturtium, Agrostis, Digitaria, Avena, Setaria, Sinapis, Lolium, Solanum, Phaseolus, Echinochloa, Scirpus, Monochoria, Sagittaria, Bromus, Alopecurus, Sorghum halepense, Rottboellia, Cyperus, Abutilon, Sida, Xanthium, Amaranthus, Chenopodium, Ipomoea, Chrysanthemum, Galium, Viola* and *Veronica*. The composition according to the invention is suitable for all methods of application convention-ally used in agriculture, e.g. pre-emergence application, post-emergence application and seed dressing. The composition according to the invention is suitable especially for controlling weeds in crops of useful plants, such as cereals, rape, sugar beet, sugar cane, plantation crops, rice, maize and soybeans, and also for non-selective weed control.

"Crops" are to be understood to mean also those crops which have been made tolerant to herbicides or classes of herbicides as a result of conventional methods of breeding or genetic engineering, for example crops that are resistant to glyphosate, HPPD-inhibitors or ALS-inhibitors.

Preferred compounds of formula I are those wherein a) $R_2$ is methyl and R is chlorine or methyl and $R_1$ is hydrogen, or b) R is chlorine or methyl and $R_1$ and $R_2$ are methyl.

Especially preferred synergistic mixtures according to the invention comprise as active ingredients a compound of formula I and either a compound of formula 2.2.a

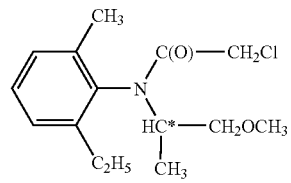

(2.2.a, aRS,1'S(−)N-(1'-methyl-2'-methoxyethyl)-N-chloroacetyl-2-ethyl-6-methylaniline), or a racemic compound of formula 2.2.b

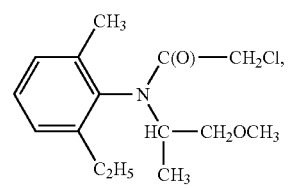

(2.2.b)

or a mixture of the compounds of formulae 2.2a and 2.2b wherein the compound of formula 2.2a is present in excess with respect to the compound of formula 2.2b, preferably in a weight ratio of from 2.5:1 to 3:1, (according to the invention such a mixture is especially used together with the safener of formula 3.1.), or a compound of formula 2.2 wherein $R_{53}$ is ethyl, $R_{54}$ is methyl and $R_{55}$ is ethoxymethyl, or a compound of formula 2.2 wherein $R_{53}$ is ethyl, $R_{54}$ is ethyl and $R_{55}$ is methoxymethyl, or a compound of formula 2.3, or a compound of formula 2.30.

Combinations of the compounds of formula I with the compound of formula 2.2a

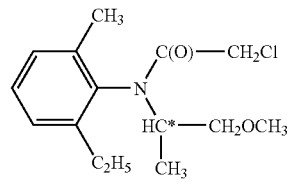

(2.2a, aRS,1'S(−)N-(1'-methyl-2'-methoxyethyl)-N-chloroacetyl-2-ethyl-6-methylaniline) and a safener of formulae 3.1 to 3.15 have been found to be especially effective compositions.

Compounds of formulae 2.1 and 2.3 to 2.13.c are known by the names imazamox, imazethapyr, imazaquin, imazapyr, dimethenamid, atrazine, terbuthylazine, simazine, terbutryn, cyanazine, ametryn, terbumeton, prohexadione calcium, sethoxydim, clethodim, tepraloxydim, flumetsulam, metosulam, pyridate, bromoxynil, ioxynil, sulcotrione, carfentrazone, sulfentrazone, isoxaflutole, glufosinate, primisulfuron, prosulfuron, rimsulfuron, halosulfuron, nicosulfuron, ethoxysulfuron, flazasulfuron and thifensulfuron and are described in the Pesticide Manual, eleventh ed., British Crop Protection Council, 1997 under the entry numbers 412, 415, 414, 413, 240, 34, 692, 651, 693, 168, 20, 691, 595, 648, 146, 49, 339, 495, 626, 88, 425, 664, 112, 665, 436, 382, 589, 613, 644, 389, 519, 287, 325 and 704. The compound of formula 2.13 wherein $Y_2$, $Y_3$ and $Y_4$ are methine, $Y_1$ is C—I, $R_{74}$ is COOMe, $Y_5$ is nitrogen, $Y_6$ is methyl and $Y_7$ is methoxy is known by the name iodosulfuron (especially the sodium salt) from AGROW No. 296, 16th Jan. 1998, page 22. The compound of formula 2.13 wherein $Y_1$, $Y_2$, $Y_3$ and $Y_4$ are methine, $R_{74}$ is trifluoromethyl, $Y_5$ is nitrogen, $Y_6$ is trifluoromethyl and $Y_7$ is methoxy is known by the name tritosulfuron and is described in DE-A-40 38 430. The compound of formula 2.13 wherein $Y_2$ is NH—CHO, $Y_1$, $Y_3$ and $Y_4$ are methine, $R_{74}$ is CONMe$_2$, $Y_5$ is methine and $Y_6$ and $Y_7$ are methoxy is known by the name foramsulfuron and is described, for example, in WO 95/29899.

The S enantiomer of the compound of formula 2.12 is registered under the CAS-Reg. No. [35597-44-5]. The compound of the general formula 2.2, aRS,1'S(−)N-(1'-methyl-2'-methoxy-ethyl)-N-chloroacetyl-2-ethyl-6-methylaniline, and a compound of the general formula 2.3, (1S,aRS)-2-chloro-N-(2,4-dimethyl-3-thienyl)-N-(2-methoxy-1-methylethyl)-acetamide, are described, for example, in WO 97/34485. The compound of formula 2.9 wherein $R_{69}$ is $NO_2$ is known by the name mesotrione and is described, for example, in U.S. Pat. No. 5,006,158. The compound of formula 2.6 wherein $R_{62}$ is ethoxy, $R_{63}$ is fluorine, Y is methine, $R_{64}$ is methoxycarbonyl, $R_{65}$ is hydrogen and $R_{66}$ is chlorine is known by the name cloransulam, for example from AGROW No. 261, 2nd Aug. 1996, page 21. The compound of formula 2.6 wherein $R_{62}$ is methoxy, $R_{63}$ is hydrogen, Y is C—F, $R_{64}$ is fluorine, $R_{65}$ is hydrogen and $R_{66}$ is fluorine is known by the name florasulam and is described in U.S. Pat. No. 5,163,995.

Furthermore, the following compounds of the composition according to the invention are described in the Pesticide Manual, eleventh ed., British Crop Protection Council, 1997:

| Compound of formula (name) | Pesticide Manual eleventh ed., Entry No.: |
| --- | --- |
| 2.14 (metribuzin) | 497 |
| 2.15 (aclonifen) | 8 |
| 2.16 (glyphosate) | 383 |
| 2.17 (bentazone) | 65 |
| 2.18 (pendimethalin) | 557 |
| 2.19 (dicamba) | 210 |
| 2.20 (butylate) | 100 |
| 2.22 (clomazone) | 150 |
| 2.23 (2,4-D) | 192 |
| 2.24 (flumiclorac) | 340 |
| 2.25 (fluthiacet-methyl) | 359 |
| 2.26 (flurtamone) | 356 |
| 2.27 (flumioxazin) | 341 |
| 2.28 (paraquat) | 550 |
| 2.29 (azafenidin) | 37 |
| 2.30 (fluthiamid) | 51 |
| 2.33 (sulfosate) | 383 |
| 2.34 (asulam) | 33 |
| 2.35 (norflurazon) | 526 |
| 2.36 (terbacil) | 689 |
| 2.37 (thiazopyr) | 702 |
| 2.38 (dithiopyr) | 259 |
| 2.39 (hexazinone) | 400 |
| 2.40 (diuron) | 260 |
| 2.41 (MCPA) | 455 |
| 2.42 (mecoprop) | 459 |
| 2.43 (tebuthiuron) | 683 |

The compound of formula 2.7 wherein $R_{67}$ is hydrogen and its preparation are described in U.S. Pat. No. 3,790,571; the compound of formula 2.6 wherein $R_{62}$ is ethoxy, Z is nitrogen, $R_{63}$ is fluorine, $R_{64}$ is chlorine, $R_{65}$ is hydrogen and $R_{66}$ is chlorine is described in U.S. Pat. No. 5,498,773. The compound of formula 2.21 and its preparation are described in U.S. Pat. No. 5,183,492; the compound of formula 2.22 is described under the name isoxachlortole in AGROW No. 296, 16th Jan. 1998, page 22. The compound of formula 2.31 is described under the name fentrazamide in The 1997 British Crop Protection Conference—Weeds, Conference Proceedings Vol. 1, 2–8, pages 67 to 72; the compound of formula 2.32 is described under the name JV 485 (isoxapropazol) in The 1997 British Crop Protection Conference—Weeds, Conference Proceedings Vol. 1, 3A-2, pages 93 to 98. The compound of formula 2.44 is known by the name pethoxamid and is described, for example, in EP-A-0 206 251. The compound of formula 2.45 is known by the name procarbazone and is described, for example, in EP-A-0 507 171; the compound of formula 2.46 is known by the name fluazolate and is described, for example, in U.S. Pat. No. 5,530,126. The compound of formula 2.47 is known by the name cinidon-ethyl and is described, for example, in DE-A-4 037 840. The compound of formula 2.48 is known by the name benzfendizone and is described, for example, in WO 97/08953. The compound of formula 2.49 is known as diflufenzopyr and is described, for example, in EP-A-0 646 315. The compound of formula 2.50 (amicarbazone) and its preparation are disclosed in DD 298 393 and in U.S. Pat. No. 5,194,085. The compound of formula 2.51 (flufenpyr-ethyl) is described in Abstracts of Papers American Chemical Society, (2000) Vol. 220, No. Part 1, pp. AGRO 174.

The composition according to the invention comprises the compound of formula I and the compounds of formulae 2.1 to 2.51 and 3.1 to 3.15 in any mixing ratio, but usually has an excess of one component over the others. Generally, the mixing ratios (ratios by weight) of the compound of formula I and the mixing partners of formulae 2.1 to 2.51 and 3.1 to 3.15 are from 1:2000 to 2000:1, especially from 200:1 to 1:200.

The rate of application may vary within wide limits and depends on the nature of the soil, the method of application (pre- or post-emergence; seed dressing; application to the seed furrow; no tillage application etc.), the crop plant, the weed to be controlled, the prevailing climatic conditions, and other factors governed by the method of application, the time of application and the target crop. The active ingredient mixture according to the invention can generally be applied at a rate of from 1 to 5000 g of active ingredient mixture/ha.

The mixtures of the compound of formula I with the compounds of formulae 2.1 to 2.51 and 3.1 to 3.15 may be used in unmodified form, that is to say as obtained in the synthesis. Preferably, however, they are formulated in customary manner, together with the adjuvants conventionally used in formulation technology, such as solvents, solid carriers or surfactants, for example into emulsifiable concentrates, directly sprayable or dilutable solutions, dilute emulsions, wettable powders, soluble powders, dusts, granules or microcapsules. As with the nature of the compositions, the methods of application, such as spraying, atomising, dusting, wetting, scattering or pouring, are chosen in accordance with the intended objectives and the prevailing circumstances.

The formulations, i.e. the compositions, preparations or mixtures comprising the compounds of formulae I and 2.1 to 2.51 and 3.1 to 3.15, and also, where appropriate, one or more solid or liquid formulation adjuvants, are prepared in a manner known per se, e.g. by intimately mixing and/or grinding the active ingredients with the formulation adjuvants, e.g. solvents or solid carriers. In addition, surface-active compounds (surfactants) may also be used in the preparation of the formulations.

Examples of solvents and solid carriers are given, for example, in WO 97/34485, page 6.

Depending on the nature of the compound of formula I to be formulated, suitable surface-active compounds are non-ionic, cationic and/or anionic surfactants and surfactant mixtures having good emulsifying, dispersing and wetting properties.

Examples of suitable anionic, non-ionic and cationic surfactants are listed, for example, in WO 97/34485, pages 7 and 8.

Also suitable in the preparation of the herbicidal compositions according to the invention are the surfactants conventionally used in formulation technology, which are described, inter alia, in "McCutcheon's Detergents and Emulsifiers Annual" MC Publishing Corp., Ridgewood N.J., 1981, Stache, H., "Tensid-Taschenbuch", Carl Hanser Verlag, Munich/Vienna, 1981 and M. and J. Ash, "Encyclopedia of Surfactants", Vol I–III, Chemical Publishing Co., New York, 1980-81.

The herbicidal formulations usually contain from 0.1 to 99% by weight, especially from 0.1 to 95% by weight, of active ingredient mixture comprising a compound of formula I together with the compounds of formulae 2.1 to 2.51 and 3.1 to 3.15 respectively, from 1 to 99.9% by weight of a solid or liquid formulation adjuvant, and from 0 to 25% by weight, especially from 0.1 to 25% by weight, of a surfactant.

Whereas commercial products are usually formulated as concentrates, the end user will normally employ dilute formulations. The compositions may also comprise further ingredients, such as stabilisers, e.g. vegetable oils or epoxidised vegetable oils (epoxidised coconut oil, rapeseed oil or soybean oil), antifoams, e.g. silicone oil, preservatives, viscosity regulators, binders, tackifiers, and also fertilisers or other active ingredients. Preferred formulations have especially the following compositions:

(%=percent by weight)

| Emulsifiable concentrates: | |
|---|---|
| active ingredient mixture: | 1 to 90%, preferably 5 to 20% |
| surfactant: | 1 to 30%, preferably 10 to 20% |
| liquid carrier: | 5 to 94%, preferably 70 to 85% |

| Dusts: | |
|---|---|
| active ingredient mixture: | 0.1 to 10%, preferably 0.1 to 5% |
| solid carrier: | 99.9 to 90%, preferably 99.9 to 99% |

| Suspension concentrates: | |
|---|---|
| active ingredient mixture: | 5 to 75%, preferably 10 to 50% |
| water: | 94 to 24%, preferably 88 to 30% |
| surfactant: | 1 to 40%, preferably 2 to 30% |

| Wettable powders: | |
|---|---|
| active ingredient mixture: | 0.5 to 90%, preferably 1 to 80% |
| surfactant: | 0.5 to 20%, preferably 1 to 15% |
| solid carrier: | 5 to 95%, preferably 15 to 90% |

| Granules: | |
|---|---|
| active ingredient mixture: | 0.1 to 30%, preferably 0.1 to 15% |
| solid carrier: | 99.5 to 70%, preferably 97 to 85% |

The following Examples illustrate the invention further, but do not limit the invention.

| F1. Emulsifiable concentrates | a) | b) | c) | d) |
|---|---|---|---|---|
| active ingredient mixture | 5% | 10% | 25% | 50% |
| calcium dodecylbenzenesulfonate | 6% | 8% | 6% | 8% |
| castor oil polyglycol ether (36 mol of ethylene oxide) | 4% | — | 4% | 4% |
| octylphenol polyglycol ether (7–8 mol of ethylene oxide) | — | 4% | — | 2% |
| cyclohexanone | — | — | 10% | 20% |
| arom. hydrocarbon mixture $C_9$—$C_{12}$ | 85% | 78% | 55% | 16% |

Emulsions of any desired concentration can be obtained from such concentrates by dilution with water.

| F2. Solutions | a) | b) | c) | d) |
|---|---|---|---|---|
| active ingredient mixture | 5% | 10% | 50% | 90% |
| 1-methoxy-3-(3-methoxy-propoxy)-propane | — | 20% | 20% | — |
| polyethylene glycol MW 400 | 20% | 10% | — | — |
| N-methyl-2-pyrrolidone | — | — | 30% | 10% |
| arom. hydrocarbon mixture $C_9$—$C_{12}$ | 75% | 60% | — | — |

The solutions are suitable for use in the form of microdrops.

| F3. Wettable powders | a) | b) | c) | d) |
|---|---|---|---|---|
| active ingredient mixture | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7–8 mol of ethylene oxide) | — | 1% | 2% | — |
| highly dispersed silicic acid | 1% | 3% | 5% | 10% |
| kaolin | 88% | 62% | 35% | — |

The active ingredient is mixed thoroughly with the adjuvants and the mixture is thoroughly ground in a suitable mill, affording wettable powders which can be diluted with water to give suspensions of any desired concentration.

| F4. Coated granules | a) | b) | c) |
|---|---|---|---|
| active ingredient mixture | 0.1% | 5% | 15% |
| highly dispersed silicic acid | 0.9% | 2% | 2% |
| inorganic carrier (Ø 0.1–1 mm) e.g. $CaCO_3$ or $SiO_2$ | 99.0% | 93% | 83% |

The active ingredient is dissolved in methylene chloride and applied to the carrier by spraying, and the solvent is then evaporated off in vacuo.

| F5. Coated granules | a) | b) | c) |
|---|---|---|---|
| active ingredient mixture | 0.1% | 5% | 15% |
| polyethylene glycol MW 200 | 1.0% | 2% | 3% |
| highly dispersed silicic acid | 0.9% | 1% | 2% |
| inorganic carrier (Ø 0.1–1 mm) e.g. CaCO$_3$ or SiO$_2$ | 98.0% | 92% | 80% |

The finely ground active ingredient is uniformly applied, in a mixer, to the carrier moistened with polyethylene glycol. Non-dusty coated granules are obtained in this manner.

| F6. Extruder granules | a) | b) | c) | d) |
|---|---|---|---|---|
| active ingredient mixture | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants, and the mixture is moistened with water. The mixture is extruded and then dried in a stream of air.

| F7. Dusts | a) | b) | c) |
|---|---|---|---|
| active ingredient mixture | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

| F8. Suspension concentrates | a) | b) | c) | d) |
|---|---|---|---|---|
| active ingredient mixture | 3% | 10% | 25% | 50% |
| ethylene glycol | 5% | 5% | 5% | 5% |
| nonylphenol polyglycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredient is intimately mixed with the adjuvants, giving a suspension concentrate from which suspensions of any desired concentration can be obtained by dilution with water.

It is often more practical for the compound of formula I and the mixing partner or partners of formulae 2.1 to 2.51 and 3.1 to 3.15 to be formulated separately and to be brought together in the desired mixing ratio in the applicator in the form of a "tank mixture" in water shortly before application.

BIOLOGICAL EXAMPLES

A synergistic effect exists whenever the action of the active ingredient combination of compounds of formula I and 2.1 to 2.51 is greater than the sum of the actions of the active ingredients applied separately.

The herbicidal action to be expected We for a given combination of two herbicides can be calculated as follows (see COLBY, S.R., "Calculating synergistic and antagonistic response of herbicide combinations", Weeds 15, pages 20–22, 1967):

$$We = X + [Y \cdot (100 - X)/100]$$

wherein:

X=percentage herbicidal action on treatment with the compound of formula I at a rate of application of p kg per hectare, compared with the untreated control (=0%).

Y=percentage herbicidal action on treatment with a compound of formula 2.1 to 2.51 at a rate of application of q kg per hectare, compared with the untreated control.

We=expected herbicidal action (percentage herbicidal action compared with the untreated control) following treatment with the compounds of formulae I and 2.1 to 2.51 at a rate of application of p+q kg of active ingredient per hectare.

When the action actually observed is greater than the value to be expected We, there is a synergistic effect.

The synergistic effect of the combinations of a compound of formula I with the compounds of formulae 2.1 to 2.51 in combination with the safeners 3.1 to 3.15 is demonstrated in the following Examples.

Experiment Description—Pre-Emergence Test

Monocotyledonous and dicotyledonous test plants are sown in standard soil in plastics pots. Directly after sowing, the test compounds are applied in aqueous suspension by spraying (500 liters of water/ha). The rates of application depend on the optimum doses ascertained under field conditions and greenhouse conditions. The test plants are then grown on in the greenhouse under optimum conditions. The tests are evaluated after 36 days (% action, 100%=plant has died, 0%=no phytotoxic action). The mixtures used in this test show good results.

Experiment Description—Post-Emergence Test

The test plants are grown to the 2- to 3-leaf stage in plastics pots under greenhouse conditions. A standard soil is used as cultivation substrate. At the 2- to 3-leaf stage, the herbicide is applied to the test plants on its own and as a mixture. The application is carried out using an aqueous suspension of the test compounds in 500 liters of water/ha. The rates of application depend on the optimum doses ascertained under field conditions and greenhouse conditions. The tests are evaluated after 33 days (% action, 100%=plant has died, 0%=no phytotoxic action). In this test, too, the mixtures used show good results.

It has been shown, surprisingly, that specific safeners are suitable for mixing with the compound of formula I. The present invention accordingly relates also to a selectively herbicidal composition for controlling grasses and weeds in crops of useful plants, especially in maize crops, that comprises a compound of formula I and a safener (counter agent, antidote) and that protects the useful plants, but not the weeds, against the phytotoxic action of the herbicide, as well as to the use of such a composition in the control of weeds in crops of useful plants.

There is accordingly also proposed in accordance with the invention a selectively herbicidal composition that, in addition to comprising customary inert formulation adjuvants, such as carriers, solvents and wetting agents, comprises as active ingredient a mixture of a) a herbicidally effective amount of the compound of formula I and b) an amount, effective for herbicide antagonism, of a compound selected from the compound of formula 3.1

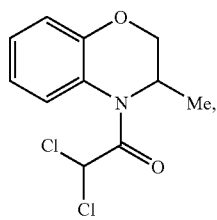
(3.1)

and the compound of formula 3.2

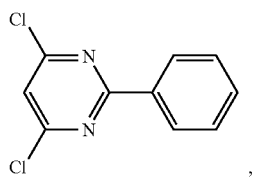
(3.2)

and the compound of formula 3.3

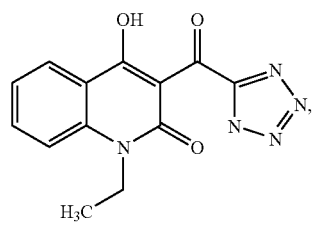
(3.3)

and the compound of formula 3.4

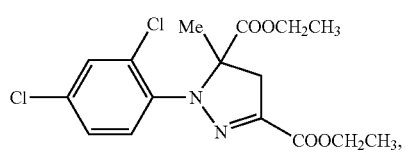
(3.4)

and the compound of formula 3.5

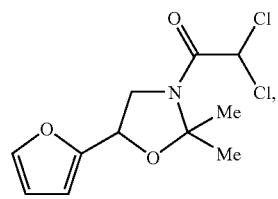
(3.5)

and the compound of formula 3.6

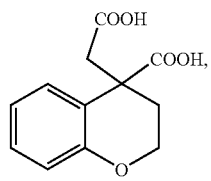
(3.6)

and the compound of formula 3.7

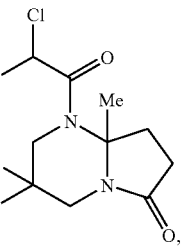
(3.7)

and the compound of formula 3.8

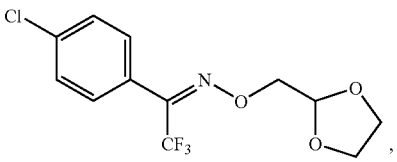
(3.8)

and of formula 3.9

$Cl_2CHCON(CH_2CH=CH_2)_2$ (3.9), and of formula 3.10

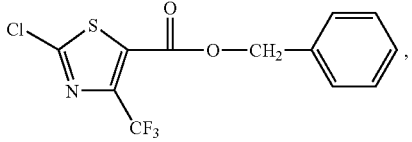
(3.10)

and of formula 3.11

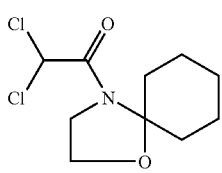
(3.11)

and of formula 3.12

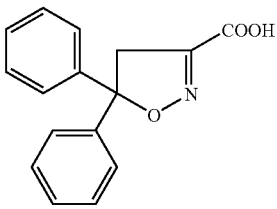

(3.12)

and its ethyl ester, and of formula 3.13

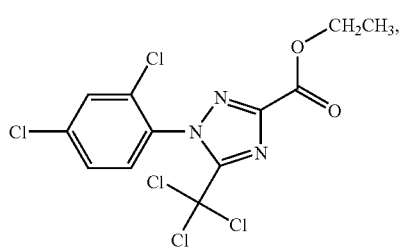

(3.13)

and of formula 3.14

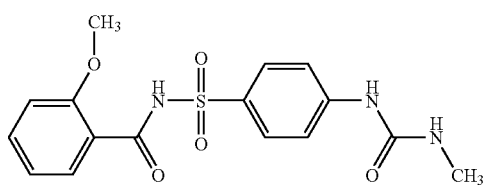

(3.14)

and of formula 3.15

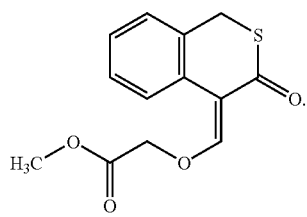

(3.15)

Preferred compositions according to the invention comprise as safener a compound selected from the compounds of formulae 3.1, 3.3 and 3.8. Those safeners are especially suitable for compositions according to the invention that comprise the above-mentioned preferred compounds of formulae 2.1 to 2.51.

Combinations of a compound of formula I with the compound of formula 3.1 have been shown to be especially effective compositions. Such a composition is preferably used together with the compound of formula 2.2a

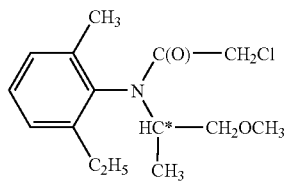

(2.2a, aRS,1'S(−)N-(1'-methyl-2'-methoxyethyl)-N-chloroacetyl-2-ethyl-6-methylaniline) or together with a mixture of the compounds of formulae 2.2a and 2.2b.

The invention relates also to a method for the selective control of weeds in crops of useful plants, which comprises treating the useful plants, seeds or cuttings thereof, or the area of cultivation thereof, with a herbicidally effective amount of the herbicide of formula I, optionally one or more herbicides selected from the compounds of formulae 2.1 to 2.51, and an amount, effective for herbicide antagonism, of a safener of formulae 3.1 to 3.15.

The compounds of formulae 3.1 to 3.15 are known and are described, for example, in the Pesticide Manual, eleventh ed., British Crop Protection Council, 1997 under entry numbers 61 (formula 3.1, benoxacor), 304 (formula 3.2, fenclorim), 462 (formula 3.4, mefenpyr-diethyl), 377 (formula 3.5, furilazol), 363 (formula 3.8, fluxofenim), 213 (formula 3.9, dichlormid) and 350 (formula 3.10, flurazole). The compound of formula 3.11 is known by the name MON 4660 (Monsanto) and is described, for example, in EP-A-0 436 483.

The compound of formula 3.6 (AC 304 415) is described, for example, in EP-A-0 613 618, and the compound of formula 3.7 in DE-A-2 948 535. The compounds of formula 3.12 are described in DE-A-4 331 448, and the compound of formula 3.13 in DE-A-3 525 205. The compound of formula 3.14 is known, for example, from U.S. Pat. No. 5,215,570 and the compound of formula 3.15 from EP-A-0 929 543. The compound of formula 3.3 is described in WO 99/00020. In addition to the compound of formula 3.3, the other 3-(5-tetrazolylcarbonyl)-2-quinolones described in WO 99/00020, especially the compounds specifically disclosed in Tables 1 and 2 on pages 21 to 29, are suitable for protecting the crop plants against the phytotoxic action of the compounds of formula I.

As crop plants that can be protected by the safeners of formulae 3.1 to 3.15 against the damaging effect of the above-mentioned herbicides there come into consideration especially cereals, cotton, soybeans, sugar beet, sugar cane, plantation crops, rape, maize and rice, more especially maize. "Crops" are to be understood to mean also those crops which have been made tolerant to herbicides or classes of herbicides as a result of conventional methods of breeding or genetic engineering, for example crops that are resistant to glyphosate, HPPD-inhibitors or ALS-inhibitors.

The weeds to be controlled may be both monocotyledonous and dicotyledonous weeds, e.g. *Stellaria, Agrostis, Digitaria, Avena, Apera, Brachiaria, Phalaris, Setaria, Sinapis, Lolium, Solanum, Echinochloa, Scirpus, Monochoria, Sagittaria, Panicum, Bromus, Alopecurus, Sorghum halepense, Sorghum bicolor, Rottboellia, Cyperus, Abutilon, Sida, Xanthium, Amaranthus, Chenopodium, Ipomoea, Chrysanthemum, Galium, Viola* and *Veronica*.

Areas of cultivation include the areas of ground on which the crop plants are already growing or which have already been sown with the seeds of those crop plants, as well as ground intended for cultivation with such crop plants.

Depending on the intended use, a safener of formula 3.1 to 3.15 can be used in the pretreatment of the seed of the crop plant (dressing of the seeds or cuttings) or can be introduced into the soil before or after sowing. It can, however, also be applied, either alone or together with the herbicide, after emergence of the plants. The treatment of the plants or seeds with the safener can therefore in principle be carried out independently of the time at which the herbicide is applied. The plants can, however, also be treated by simultaneous application of herbicide and safener (e.g. in the form of a tank mixture). The ratio of the rate of application of safener to the rate of application of herbicide depends largely on the method of application. In the case of field treatment, which is carried out either using a tank mixture comprising a combination of safener and herbicide or by separate application of safener and herbicide, the ratio of herbicides to safener is generally from 100:1 to 1:10, preferably from 20:1 to 1:1. In the case of field treatment it is usual to apply from 0.001 to 1.0 kg of safener/ha, preferably from 0.001 to 0.25 kg of safener/ha.

The rate of application of herbicides is generally from 0.001 to 5 kg/ha, but preferably from 0.005 to 0.5 kg/ha.

The compositions according to the invention are suitable for all methods of application conventionally used in agriculture, e.g. pre-emergence application, post-emergence application and seed dressing.

In the case of seed dressing, generally from 0.001 to 10 g of safener/kg of seed, preferably from 0.05 to 2 g of safener/kg of seed, are applied. When the safener is applied in liquid form shortly before sowing, with soaking of the seeds, then advantageously the safener solutions used contain the active ingredient in a concentration of from 1 to 10 000 ppm, preferably from 100 to 1000 ppm.

For the purpose of application, the safeners of formulae 3.1 to 3.15 or combinations of those safeners with the herbicide of formula I and, as appropriate, one or more herbicides selected from formulae 2.1 to 2.51 are advantageously formulated together with adjuvants customary in formulation technology, e.g. into emulsifiable concentrates, coatable pastes, directly sprayable or dilutable solutions, dilute emulsions, wettable powders, soluble powders, dusts, granules or microcapsules.

Such formulations are described, for example, in WO 97/34485, pages 9 to 13. The formulations are prepared in known manner, e.g. by intimately mixing and/or grinding the active ingredients with liquid or solid formulation adjuvants, e.g. solvents or solid carriers. In addition, surface-active compounds (surfactants) can also be used in the preparation of the formulations. Solvents and solid carriers suitable for that purpose are mentioned, for example, in WO 97/34485, page 6.

Depending on the nature of the compounds of formulae I, 2.1 to 2.51 and 3.1 to 3.15 to be formulated, there come into consideration as surface-active compounds non-ionic, cationic and/or anionic surfactants and surfactant mixtures having good emulsifying, dispersing and wetting properties. Examples of suitable anionic, non-ionic and cationic surfactants are listed, for example, on pages 7 and 8 of WO 97/34485. Also suitable for the preparation of the herbicidal compositions according to the invention are the surfactants conventionally employed in formulation technology, which are described, inter alia, in "McCutcheon's Detergents and Emulsifiers Annual" MC Publishing Corp., Ridgewood N.J., 1981, Stache, H., "Tensid-Taschenbuch", Carl Hanser Verlag, Munich/Vienna, 1981 and M. and J. Ash, "Encyclopedia of Surfactants", Vol. I–III, Chemical Publishing Co., New York, 1980-81.

The herbicidal formulations usually contain from 0.1 to 99% by weight, especially from 0.1 to 95% by weight, of active ingredient mixture comprising a compound of formula I, a compound selected from the compounds of formulae 2.1 to 2.51 and the compounds of formulae 3.1 to 3.15, from 1 to 99.9% by weight of a solid or liquid formulation adjuvant and from 0 to 25% by weight, especially from 0.1 to 25% by weight, of a surfactant. Whereas commercial products are usually formulated as concentrates, the end user will normally employ dilute formulations.

The compositions may also comprise further ingredients, such as stabilisers, e.g. vegetable oils or epoxidised vegetable oils (epoxidised coconut oil, rapeseed oil or soybean oil), anti-foams, e.g. silicone oil, preservatives, viscosity regulators, binders, tackifiers, and also fertilisers or other active ingredients. For the use of safeners of formulae 3.1 to 3.15, or of compositions comprising them, in the protection of crop plants against the damaging effects of herbicides of formulae I and 2.1 to 2.51, various methods and techniques come into consideration, such as, for example, the following:

i) Seed Dressing a) Dressing of the seeds with a wettable powder formulation of a compound of formulae 3.1 to 3.15 by shaking in a vessel until uniformly distributed over the seed surface (dry dressing). In that procedure approximately from 1 to 500 g of compound of formulae 3.1 to 3.15 (4 g to 2 kg of wettable powder) are used per 100 kg of seed.

b) Dressing of the seeds with an emulsifiable concentrate of a compound of formulae 3.1 to 3.15 according to method a) (wet dressing).

c) Dressing by immersing the seeds for from 1 to 72 hours in a liquor comprising from 100 to 1000 ppm of a compound of formulae 3.1 to 3.15 and optionally subsequently drying the seeds (immersion dressing).

Dressing the seed or treating the germinated seedling are naturally the preferred methods of application, because treatment with the active ingredients is directed entirely at the target crop. Generally from 1 to 1000 g of antidote, preferably from 5 to 250 g of antidote, are used per 100 kg of seed, but depending on the methodology, which also allows other active ingredients or micronutrients to be added, concentrations above or below the limits indicated may be employed (repeat dressing).

ii) Application as a Tank Mixture

A liquid formulation of a mixture of antidote and herbicide is used (ratio by weight of the one to the other from 10:1 to 1:100), the rate of application of herbicide being from 0.005 to 5.0 kg per hectare. Such tank mixtures are applied before or after sowing.

iii) Application to the Seed Furrow

The compounds of formulae 3.1 to 3.15 are introduced into the open, sown seed furrow in the form of an emulsifiable concentrate, wettable powder or granules. Once the seed furrow has been covered over, the herbicide is applied in the usual manner pre-emergence.

iv) Controlled Release of Active Ingredient

The compounds of formulae 3.1 to 3.15 are applied in solution to mineral granule carriers or polymerised granules (urea/formaldehyde) and dried. If desired, it is also possible to apply a coating that allows the active ingredient to be released in metered amounts over a specific period of time (coated granules).

Preferred formulations have especially the following compositions:

(%=percent by weight)

Emulsifiable concentrates:

| | |
|---|---|
| active ingredient mixture: | 1 to 90%, preferably 5 to 20% |
| surfactant: | 1 to 30%, preferably 10 to 20% |
| liquid carrier: | 5 to 94%, preferably 70 to 85% |

Dusts:

| | |
|---|---|
| active ingredient mixture: | 0.1 to 10%, preferably 0.1 to 5% |
| solid carrier: | 99.9 to 90%, preferably 99.9 to 99% |

Suspension concentrates:

| | |
|---|---|
| active ingredient mixture: | 5 to 75%, preferably 10 to 50% |
| water: | 94 to 24%, preferably 88 to 30% |
| surfactant: | 1 to 40%, preferably 2 to 30% |

Wettable powders:

| | |
|---|---|
| active ingredient mixture: | 0.5 to 90%, preferably 1 to 80% |
| surfactant: | 0.5 to 20%, preferably 1 to 15% |
| solid carrier: | 5 to 95%, preferably 15 to 90% |

Granules:

| | |
|---|---|
| active ingredient mixture: | 0.1 to 30%, preferably 0.1 to 15% |
| solid carrier: | 99.5 to 70%, preferably 97 to 85% |

The following Examples illustrate the invention further, but do not limit the invention. Formulation Examples for mixtures of herbicides of formula I, optionally herbicides of formulae 2.1 to 2.51, and safeners of formulae 3.1 to 3.15 (%=percent by weight)

| F1. Emulsifiable concentrates | a) | b) | c) | d) |
|---|---|---|---|---|
| active ingredient mixture | 5% | 10% | 25% | 50% |
| calcium dodecylbenzenesulfonate | 6% | 8% | 6% | 8% |
| castor oil polyglycol ether (36 mol of ethylene oxide) | 4% | — | 4% | 4% |
| octylphenol polyglycol ether (7–8 mol of ethylene oxide) | — | 4% | — | 2% |
| cyclohexanone | — | — | 10% | 20% |
| arom. hydrocarbon mixture $C_9$—$C_{12}$ | 85% | 78% | 55% | 16% |

Emulsions of any desired concentration can be obtained from such concentrates by dilution with water.

| F2. Solutions | a) | b) | c) | d) |
|---|---|---|---|---|
| active ingredient mixture | 5% | 10% | 50% | 90% |
| 1-methoxy-3-(3-methoxy-propoxy)-propane | — | 20% | 20% | — |
| polyethylene glycol MW 400 | 20% | 10% | — | — |
| N-methyl-2-pyrrolidone | — | — | 30% | 10% |
| arom. hydrocarbon mixture $C_9$—$C_{12}$ | 75% | 60% | — | — |

The solutions are suitable for use in the form of microdrops.

| F3. Wettable powders | a) | b) | c) | d) |
|---|---|---|---|---|
| active ingredient mixture | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7–8 mol of ethylene oxide) | — | 1% | 2% | — |
| highly dispersed silicic acid | 1% | 3% | 5% | 10% |
| kaolin | 88% | 62% | 35% | — |

The active ingredient is mixed thoroughly with the adjuvants and the mixture is thoroughly ground in a suitable mill, affording wettable powders which can be diluted with water to give suspensions of any desired concentration.

| F4. Coated granules | a) | b) | c) |
|---|---|---|---|
| active ingredient mixture | 0.1% | 5% | 15% |
| highly dispersed silicic acid | 0.9% | 2% | 2% |
| inorganic carrier (Ø 0.1–1 mm) e.g. $CaCO_3$ or $SiO_2$ | 99.0% | 93% | 83% |

The active ingredient is dissolved in methylene chloride and applied to the carrier by spraying, and the solvent is then evaporated off in vacuo.

| F5. Coated granules | a) | b) | c) |
|---|---|---|---|
| active ingredient mixture | 0.1% | 5% | 15% |
| polyethylene glycol MW 200 | 1.0% | 2% | 3% |
| highly dispersed silicic acid | 0.9% | 1% | 2% |
| inorganic carrier (Ø 0.1–1 mm) e.g. $CaCO_3$ or $SiO_2$ | 98.0% | 92% | 80% |

The finely ground active ingredient is uniformly applied, in a mixer, to the carrier moistened with polyethylene glycol. Non-dusty coated granules are obtained in this manner.

| F6. Extruder granules | a) | b) | c) | d) |
|---|---|---|---|---|
| active ingredient mixture | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants, and the mixture is moistened with water. The mixture is extruded and then dried in a stream of air.

| F7. Dusts | a) | b) | c) |
|---|---|---|---|
| active ingredient mixture | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

| F8. Suspension concentrates | a) | b) | c) | d) |
|---|---|---|---|---|
| active ingredient mixture | 3% | 10% | 25% | 50% |
| ethylene glycol | 5% | 5% | 5% | 5% |
| nonylphenol polyglycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredient is intimately mixed with the adjuvants, giving a suspension concentrate from which suspensions of any desired concentration can be obtained by dilution with water.

It is often more practical for the compounds of formulae I, 2.1 to 2.51 and 3.1 to 3.15 to be formulated separately and then to be brought together in the desired mixing ratio in the applicator in the form of a "tank mixture" in water shortly before application.

The ability of the safeners of formulae 3.1 to 3.15 to protect crop plants against the phytotoxic action of herbicides of formula I is illustrated in the following Examples.

Biological Example: Safening Action

The test plants are grown in plastics pots under greenhouse conditions to the 4-leaf stage. At that stage, either the herbicides alone or the mixtures of the herbicides with the test compounds being tested as safeners are applied to the test plants. The application is in the form of an aqueous suspension of the test compounds prepared from a 25% wettable powder (Example F3, b)) with 500 liters of water/ha. 4 weeks after application, the phytotoxic action of the herbicides on the crop plants, e.g. maize and cereals, is evaluated using a percentage scale. 100% denotes that the test plant has died, 0% denotes no phytotoxic action. The mixtures according to the invention show good action in this test.

What is claimed is:

1. A selectively herbicidal composition that, in addition to comprising inert formulation adjuvants, comprises as active ingredient a mixture of a) a herbicidally effective amount of a first compound having the formula:

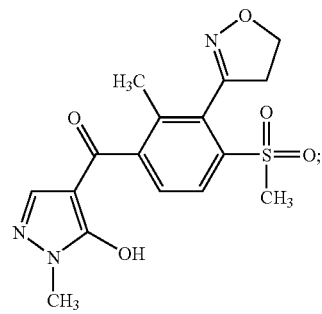

b) a synergistically effective amount of a second compound of formula 2.2a

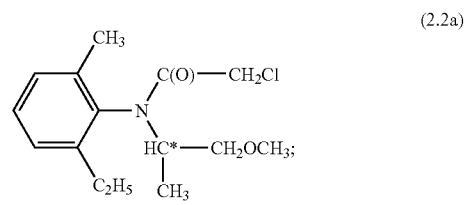

(2.2a)

having the chemical designation aRS,1'S(−)N-(1'-methyl-2'-methoxyethyl)-N-chloroacetyl-2-ethyl-6-methylaniline), and c) an amount, effective for herbicide antagonism, of a third compound having the formula 3.1:

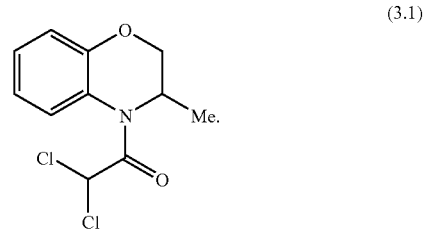

(3.1)

2. A method of controlling undesired plant growth in crops of useful plants, which comprises allowing a herbicidally effective amount of a composition according to claim 1 to act on the crop plant or the locus thereof.

3. A method according to claim 2, wherein the crop plant is maize or sugar cane.

4. A method according to claim 2, wherein the crops of useful plants are treated with said composition at rates of application corresponding to a total amount of active ingredient of from 1 to 5000 g per hectare.

* * * * *